United States Patent
Gilar et al.

(10) Patent No.: US 8,153,009 B2
(45) Date of Patent: Apr. 10, 2012

(54) APPARATUS AND METHODS FOR MASS-SPECTROMETRIC DIRECTED PURIFICATION OF BIOPOLYMERS

(75) Inventors: Martin Gilar, Franklin, MA (US); John C. Gebler, Hopkinton, MA (US); Fang Xia, Moorpark, CA (US)

(73) Assignee: Waters Technologies Corporation, Milford, MA (US)

( * ) Notice: Subject to any disclaimer, the term of this patent is extended or adjusted under 35 U.S.C. 154(b) by 971 days.

(21) Appl. No.: 11/912,047

(22) PCT Filed: Apr. 21, 2006

(86) PCT No.: PCT/US2006/015060
§ 371 (c)(1),
(2), (4) Date: Jun. 11, 2008

(87) PCT Pub. No.: WO2006/116064
PCT Pub. Date: Nov. 2, 2006

(65) Prior Publication Data
US 2008/0283739 A1    Nov. 20, 2008

Related U.S. Application Data

(60) Provisional application No. 60/674,051, filed on Apr. 22, 2005.

(51) Int. Cl.
*B01D 15/08* (2006.01)
(52) U.S. Cl. .................. 210/656; 210/198.2
(58) Field of Classification Search .......... 210/635, 210/656, 659, 198.2
See application file for complete search history.

(56) References Cited

U.S. PATENT DOCUMENTS

| | | | |
|---|---|---|---|
| 5,427,686 A | 6/1995 | Asher | |
| 5,439,591 A | 8/1995 | Pliura et al. | |
| 5,449,461 A | 9/1995 | Ito | |
| 5,478,924 A | 12/1995 | Cramer et al. | |
| 5,545,328 A | 8/1996 | Pliura et al. | |
| 5,851,400 A | 12/1998 | Frey et al. | |
| 6,245,238 B1 | 6/2001 | Agner | |
| 6,265,542 B1 | 7/2001 | Fahrner et al. | |
| 6,379,554 B1 | 4/2002 | Kearney et al. | |
| 6,413,431 B1 * | 7/2002 | Abedi | 506/6 |
| 6,576,134 B1 | 6/2003 | Agner | |
| 6,602,420 B2 | 8/2003 | Kearney et al. | |
| 2004/0035789 A1 | 2/2004 | Wheat et al. | |

OTHER PUBLICATIONS

Deshmukh, et al; Application of sample displacement techniques to the purification of synthetic oligonucleotides and nucleic acids: a mini-review with experimental results; Journal of Chromatography A, 806 (1998) 77-9.

(Continued)

*Primary Examiner* — Ernest G Therkorn
(74) *Attorney, Agent, or Firm* — Jamie H. Rose

(57) ABSTRACT

A method for extracting at least one target compound from a sample includes injecting an overloaded amount of the sample into a chromatographic conduit (110), and flowing a solvent having a time-varying composition through the conduit (110). An apparatus for extracting at least one target compound from a sample includes a chromatography module, a mass-spectrometry module in fluid communication with the chromatography module to receive a portion of an eluent from the chromatography module, and a control unit in communication with the chromatography module and the mass-spectrometry module.

21 Claims, 6 Drawing Sheets

OTHER PUBLICATIONS

Kalghatgi, et al; Rapid displacement chromatography of melittin on micropellicular octadecyl-silica; Journal of Chromatography, 604 (1992) 47-53.

Hodges, et al; Multi-column preparative reversed-phase sample displacement chromatography of peptides; Journal of Chromatography, 548 (1991) 267-280.

Ajay Lajmi; Pall Life Sciences; apping the Potential of Antisense Drugs, Feb. 2005, 12-18.

Hodges, et al; Preparative Purification of Peptides by Reversed-Phase Chromatography; Sample Displacement Mode Versus Gradient Elution Mode; Journal of Chromatography, 444 (1988) 349-362.

Husband, et al; Development of simultaneous purification methodology for multiple synthetic peptides by reversed-phase sample displacement chromatography; Journal of Chromatography A, 893 (2000) 81-94.

Horvath, et al; High-Performance Displacement Chromatography; Journal of Chromatography, 218 (1981) 365-393.

\* cited by examiner

Displacement train

Solvent Gradient
(% mobile-phase B)

APPARATUS AND METHODS FOR MASS-SPECTROMETRIC DIRECTED PURIFICATION OF BIOPOLYMERS

CROSS REFERENCED RELATED APPLICATION INFORMATION

This application is the National Stage of International Application No. PCT/US2006/015060, filed on Apr. 21, 2006, which claims priority to and benefit of U.S. Provisional Patent Application Ser. No. 60/674,051, filed on Apr. 22, 2005. The entire contents of these applications are incorporated herein by reference.

TECHNICAL FIELD

The invention generally relates to chromatography, and, more particularly, to instruments and methods for chromatographic-based separations of target and byproduct materials.

BACKGROUND INFORMATION

In many scientific or industrial applications, compounds are purified for testing, analysis, or volume production. Purification of a compound involves separating a desired compound from a mixture that contains additional compounds and/or impurities.

Chromatography is a method for fractionating a mixture to separate compounds of the mixture, and at times is used for purification. In liquid chromatography, for example, a sample containing a number of compounds to be separated is injected into a fluid stream (i.e., a solvent,) and directed through a chromatographic column. The column separates the mixture into its component species in response to differential retention of the component species in the column. Concentration peaks associated with the separated compounds typically emerge in sequence from the column.

The chromatographic peaks are often characterized with respect to their retention time, that is, the time in which the center of the band transits the detector relative to the time of injection. In many applications, the retention time of a peak is used to infer the identity of the eluting analyte based upon related analyses incorporating standards or calibrants. The presence of the separated species are often distinguished through use of a refractometer or an absorbtometer utilizing ultraviolet (UV) light.

A typical high-performance liquid chromatography (HPLC) system includes a pump for delivering a fluid (a "mobile phase") at a controlled flow rate and composition, an injector to introduce a sample solution into the flowing mobile phase, a tubular column encasement containing a packing material or sorbent (a "stationary phase"), and a UV detector to register the presence and amount of the sample compounds in the mobile phase. The presence of a particular compound in the mobile phase exiting the column is then detected by measuring changes in physical or chemical properties of the eluent. Response peaks corresponding to the presence of each of the compounds of the sample can be observed and recorded by tracking the detector's signal over time.

For target purification, it is often desirable to recover the target compound with as high a purity as possible, and to separate the largest possible quantity of a sample with each run to reduce labor, run time, and other costs. Typical chromatography systems, however, have sample load limits. In some cases, use of overloaded samples provides increased processing volumes. Overloading, however, typically involves increased complexity in extraction of a target compound through use of a displacer material or a segmented column. Moreover, the extracted target often has less than a desired purity.

SUMMARY OF THE INVENTION

The invention arises, in part, from the realization that one or more compounds can be more efficiently separated from a chromatography sample via use of gradient-mode elution in combination with displacement separation, i.e., use of a solvent composition that varies in time in combination with overloaded sample conditions. Some advantageous embodiments also utilize sample-displacement, i.e., no separate displacer material is added to the sample compounds. Additional embodiments also utilize a mass spectrometer or other suitable detector to provide good resolution of eluting compounds to permit accurate observation of boundaries between the eluting sample compounds. Some embodiments of the invention provide extraction windows that permit efficient collection of target compounds having a relatively high purity after a single pass through a chromatography column.

Thus, in some embodiments, boundaries between compounds in a self-displacement train remain substantially distinct even though a flowing solvent composition has a composition gradient. In some of these embodiments, the solvent acts as a displacer to urge the separated compounds through a column. Thus, in contrast to some prior methods, for example, a separate displacer material, or separable column sections, or multiple columns need not be utilized to extract a separated target compound.

In many of these embodiments, UV detection would typically have insufficient resolution to sufficiently distinguish compound boundaries under overloaded sample conditions. These embodiments, however, utilize a suitable analytical technique, such as mass spectrometry, for accurate identification of a boundary between compounds in a displacement train.

The observed onset of a mass-spectral peak for a desired sample compound is used, in one example embodiment, to responsively commence collection of the target compound. Similarly, collection is optionally ceased in response to detection of the end of the mass-spectral peak, which indicates that the desired compound is no longer eluting.

Accordingly, one embodiment of the invention features a method for extracting at least one target compound from a sample including a plurality of compounds. The method includes injecting an overloaded amount of the sample into a chromatographic conduit, and flowing a solvent having a time-varying composition through the conduit. In response to injecting the sample, a displacement train forms, in which the at least one target compound is substantially separated from a contiguous compound of the plurality of compounds. In response to flowing the solvent, an eluent including the at least one target compound elutes from an exit orifice of the conduit while the at least one target compound remains substantially separated from the contiguous compound.

A second embodiment of the invention features a method for extracting at least one target compound from a sample. The method includes injecting an overloaded amount of the sample into a chromatographic conduit, causing an eluent including the at least one target compound to elute from an exit orifice of the conduit, obtaining mass-spectroscopic data that identifies a boundary between the at least one target compound and the contiguous compound, and collecting the at least one target compound in response to the identified boundary. The mass-spectroscopic data is obtained from a portion of the eluent.

Another embodiment of the invention features an apparatus for extracting at least one target compound from a sample. The apparatus includes a chromatography module, a mass-spectrometry module in fluid communication with the chromatography module to receive a portion of an eluent from the chromatography module, and a control unit in communication with the chromatography module and the mass-spectrometry module. The control unit includes at least one processor and at least one memory for storing a plurality of instructions that, when executed by the at least one processor, causes implementation of the steps of injecting an overloaded amount of the sample into a chromatographic conduit of the chromatography module, flowing a solvent having a time-varying composition to cause elution of material including the at least one target compound, and collecting the at least one target compound in response to mass-spectrometry data associated with the portion of the eluted material.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1b is a diagram of a square-wave concentration profile of separated compounds and a solvent gradient profile associated with FIG. 1a;

FIG. 2b is a graph of a UV chromatogram and mass-spectral ion chromatograms for three compounds of a 100 µg sample associated with FIG. 2a;

DESCRIPTION

The suffix "mer," as used herein, indicates a member of a class that can join with other members to form a polymer chain, e.g., a dimer, trimer, decamer, 30-mer, etc. For example, members of the class of nucleotides, when bonded together, can form an oligonucleotide, and members of the class of peptides can bond together to form polypeptides or proteins.

The phrase "chromatographic system" herein refers to equipment to perform chemical separations. These systems typically move fluids under pressure. Some embodiments of the invention involve chromatographic-system modules that are placed in fluid communication with mass spectrometers through interfaces. These interfaces at times create or maintain separated materials in an ionic form and typically place a stream of fluid containing the ions into an atmosphere where the stream is vaporized and the ions are received in an orifice of the mass spectrometer. The orifice typically separates low-pressure chambers of the mass spectrometer from an atmospheric-pressure interface.

The phrase "loading capacity" herein refers to a threshold for the maximum volume and/or maximum mass of a sample that may be loaded into a column without causing substantial peak broadening and/or formation of a displacement train of separated compounds and/or loss of UV detector resolution. A "displacement train" herein refers to the group of physically separated, but closely spaced or overlapping, compounds that forms in response to overloading a sample in a column; each compound in the train typically has some breadth corresponding to its quantity in the sample. "Self displacement" and "sample displacement" herein refer to use of an overloaded sample to create a displacement train without use of a displacer material, in addition to the sample and solvent, to urge the sample compounds through a column. As described below, various embodiments of the invention provide relatively good separation of compounds and mass-spectrometry resolution of displacement-train compound boundaries.

The phrase "isocratic mode of chromatography" herein refers to the use of a solvent composition that remains substantially constant as a function of time. During isocratic-mode chromatography, analytes in some samples elute while a fixed-concentration mobile phase flows through a column.

The phrase "gradient mode of chromatography" herein refers to a flowing solvent composition that changes as a function of time, typically in response to a user defined profile. A solvent has a composition that is, for example, a mixture of two solutions, referred to herein as mobile-phase A and mobile-phase B.

Solution concentrations, as understood by one having ordinary skill, can be expressed as molar solutions. A "1 M" solution, for example, is a 1 mole/liter solution. Similarly, a "1 mM" solution is a 1 millimole/liter solution.

Figure 1A:
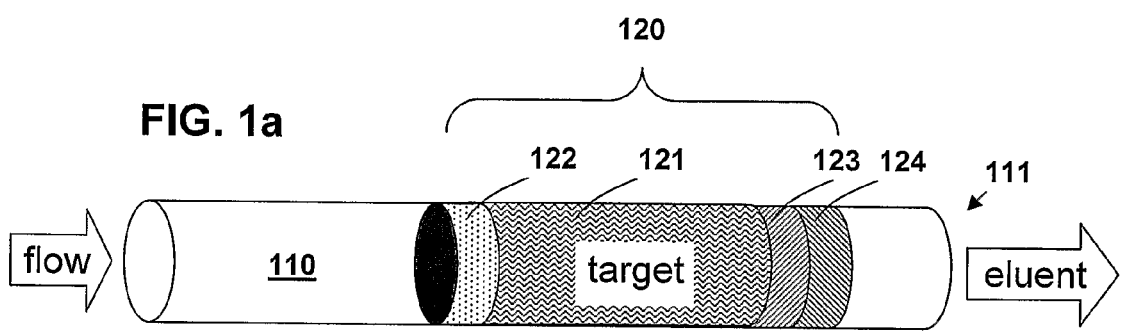
FIG. 1a is a schematic diagram of a chromatographic column containing an overloaded sample moving through the column in response to a flowing solvent having a gradient, in accordance with one embodiment of the invention.
Figure 1B:
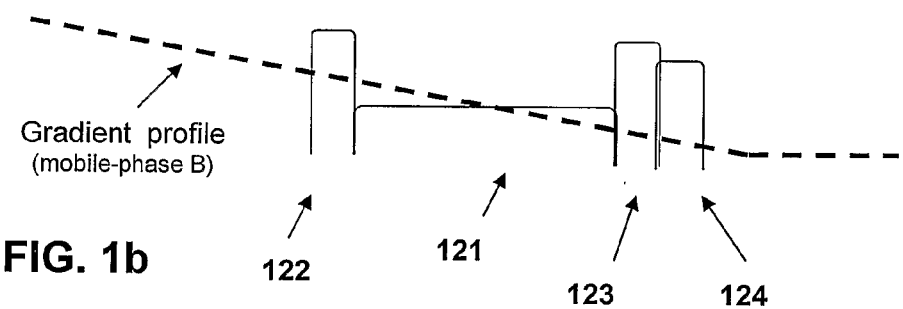
Figure 1C:
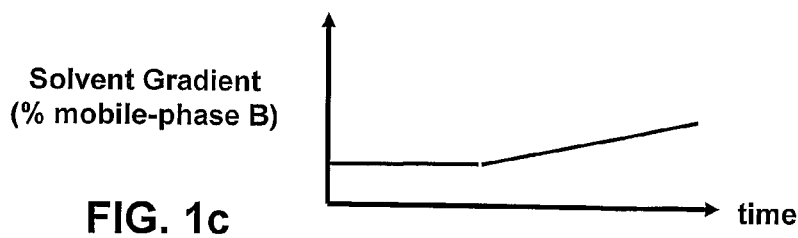
FIG. 1c is a graph of solvent composition versus time associated with the solvent gradient profile of FIG. 1b.

Now referring to FIG. 1a, FIG. 1b, and FIG. 1c, a method for extracting at least one target compound from a sample including a plurality of compounds is described, in accordance with one embodiment of the invention. The method involves use of overloading and use of a flowing solvent having a varying composition to cause elution of the separated sample.

FIG. 1a is a schematic illustration of a chromatographic column 110 containing an overloaded sample 120 moving through the column 110 in response to a gradient-mode flowing solvent. The column contains a sorbent and includes an exit orifice 111 from which eluent exits the column. As illustrated, the overloaded sample has separated and formed a self-displacement train in the column 120. The displacement train 120 includes a target compound 121 and non-target compounds 122, 123, 124, which are, for example, byproduct compounds.

FIG. 1b is a diagram, associated with FIG. 1b, which qualitatively illustrates a square-wave zone concentration profile of the separated compounds of the sample, as well as a concentration gradient profile of the solvent as a function of position along the column 110. The diagram illustrates sample-self displacement in which the sample's more weakly retained compounds have been displaced from the chromatographic sorbent by more strongly retained compounds.

In view of the description herein, one of ordinary skill will understand that the illustrated gradient profile is merely qualitative. For example, the profile qualitatively illustrates a gradient that is linear (increasing at a constant rate) after an initial period of isocratic solvent flow. At a particular point in time during processing, however, the isocratic solvent composition can exist throughout the conduit 110, or, for example, the solvent composition can be nearly constant throughout the conduit 110, depending on the flow rate and the duration of transit of the displacement train 120 through the conduit 110.

FIG. 1c is a graph of solvent composition versus time associated with the solvent gradient profile of FIG. 1b. As illustrated, the composition in this embodiment is initially isocratic—used, for example, to inject the sample in to the conduit 120, and, for example, during formation of the displacement train 120. Subsequently, the solvent composition has a linear gradient. Generally, throughout this description, solvent composition is expressed in terms of a percentage of one solvent component of two or more solvent components. Many solvents embodiments include an A-phase component and a B-phase component. For such embodiments described herein, solvent composition is expressed in terms of the B-phase component.

FIGS. 1a, 1b, and 1c illustrate a method for extracting at least one target compound, such as the compound 121 illustrated in FIG. 1a, from a sample including a plurality of compounds 121, 122, 123, 124, in accordance with one embodiment of the invention. The method includes injecting an overloaded amount of the sample into a chromatographic conduit 110, and, in response, forming a displacement train 120 in which the at least one target compound 121 is substantially separated from a contiguous compound 122, 123 of the plurality of compounds 122, 123, 124. The method also includes flowing, through the conduit 110, a solvent having a time-varying composition; in response, an eluent that includes the at least one target compound 121 elutes from an exit orifice 111 of the conduit 110. The at least one target compound 121 remains substantially separated from the contiguous compound 122, 123.

The method employs any suitable chromatographic technique, including, for example, reverse-phase HPLC and/or ion-exchange HPLC. A conduit is, for example, a chromatographic column of a size selected to support a desired production rate. Referring now to Table 1, examples of suitable column dimensions and mass loads are illustrated. Table 1 is a listing of some suitable illustrative mass loads and solvent flow rates for several column inner diameters (ID's).

TABLE 1

| Column ID (mm) | Mass Load (overload) | Solvent Flow Rate (mL/min) |
| --- | --- | --- |
| 4.6 | 20 mg | 1 |
| 10.0 | 100 mg | 5 |
| 19.0 | 340 mg | 17 |
| 30.0 | 0.85 g | 43 |
| 50.0 | 2.4 g | 118 |

These illustrative values are not intended to limit application of the invention to the use of columns of a particular size and/or solvent of a particular flow rate. As illustrated, the method provides as much as a 20-fold increase in sample volume, or more, in comparison to some prior elution-chromatography purification methods.

The solvent gradient is selected from any suitable solvent gradient. For example, in one illustrative embodiment, the gradient is linear and shallow. In this example, the gradient is ramped gradually such that, at any one time, the solvent composition is nearly constant along the length of the conduit. Moreover, in some embodiments, an isocratic solvent is initially used, to inject the sample into a column and form the displacement train of separated compounds. A time-varying solvent composition is then used to cause the displacement train to move through the column and elute from a column exit.

Some suitable solvents and gradient profiles are described in more detail below. The described solvents are not intended to limit application of the invention to any particular gradient profile. Other embodiments of the invention utilize non-linear gradients and/or solvent concentration gradients that vary more rapidly or less rapidly. In some embodiments, a size of a gradient is selected to avoid causing an overlap between neighboring zones greater than a desired amount of overlap.

In some alternative embodiments of the above-described method, a column includes a particulate sorbent material. The sorbet material is selected from any suitable sorbent material, including known materials such as silica or a mixture of silica and a copolymer such as an alkyl compound. The sorbent is selected, for example, to support development of a displacement train having well-separated compounds that remain well-separated during solvent elution under gradient conditions.

A sorbent particle size and/or size distribution are suitably chosen. For example, in some implementations, a particle diameter is chosen to be small enough to support preservation of well-separated compounds in a wave train. In some implementations, a suitable particle diameter is approximately 5 µm or less.

Moreover, some embodiments advantageously utilize porous sorbent material(s), such as porous versions silica or silica mixtures. A suitable pore size for samples containing large molecules, for example, is, for example, approximately 10 nm to approximately 30 nm. For some separations, a particular porous material(s) is chosen to provide a desired compound diffusion behavior. For example, a porous sorbent is selected in some embodiments to provide a diffusion coefficient for a relatively large target molecule that is 10 to $10^2$ times smaller than a diffusion coefficient for smaller molecules. Or, for example, a smaller pore size is selected to provide improved separation between contiguous compounds in a displacement train.

The method, in one alternative embodiment, includes collection of spectroscopic data from the eluent, for example, a diverted portion of the eluent. The spectroscopic data identifies a boundary between the at least one target compound and the contiguous compound. The spectroscopic data optionally is used to identify a starting and an ending boundary of a target compound to assist collection of the target compound.

The spectroscopic data is preferably collected via a technique that provides suitable resolution under overloaded sample conditions. One suitable technique is mass spectrometry, for example, electrospray-ionization mass spectrometry (ESI-MS). Thus, optionally, a small portion of the eluent is diverted to a mass spectrometer. In some embodiments, one or more target compounds are collected from the remainder of the eluent in response to identification of collection windows, as supported by mass-spectrometric data. A collected target compound, in some embodiments of the invention, has a purity of approximately 98% or better after a single chromatographic processing step.

Various embodiments also provide excellent yields of target compounds. Such embodiments provide accurate selection of collection windows, thus supporting efficient collection of a purified compound. For example, a target compound can be extracted from a sample at a yield of approximately 80% or better, or 90% or better. Thus, some embodiments provide both excellent yield and high purity after a single processing run of a chromatographic module.

Some embodiments of the invention are utilized to automate the purification of target biopolymers, such as synthetic peptides and oligonucleotides. Various column sizes are used, under overloaded conditions, in response to a desired quantity of purified target material.

In the following, some illustrative examples of target compound purification, in accordance with some embodiments of the invention, are described. These examples are not intended to limit application of the invention. Alternative implementations will be apparent to one having ordinary skill in the separation arts. The following illustrative examples were obtained with the following described samples, materials, and instrumentation.

Samples—synthetic 25-mer phosphorothioate (PS) oligonucleotide (available from Hybridon, Inc., Cambridge, Mass.), and synthetic peptides (available from Cell Essentials, Boston, Mass., and from SynPep, Dublin, Calif.).

Solvents—for oligonucleotides, a solvent mobile-phase A included 100 mM hexafluoroisopropanol (HFIP) and 8.6 mM triethylamine (TEA), adjusted to pH 8.3, and a solvent mobile-phase B included 100% methanol (MeOH.) For peptides, a solvent mobile-phase A included 0.1% trifluoroacetic acid (TFA) in water, and a solvent mobile-phase B included of 0.08% TFA in acetonitrile (ACN).

Chromatographic separations—capillary separations were performed via HPLC with a CAPLC® separations module equipped with a 2996 photodiode array (PDA) detector (available from Waters Corporation, Milford, Mass.). Analytical separations were performed on an ALLIANCE® bio-separations system equipped with a 2996 PDA detector (available from Waters Corporation, Milford, Mass.).

Mass spectrometry—spectrometry was performed with a MICROMASS® LCT™ mass spectrometer (available from Waters Corporation, Milford, Mass.) for analysis of oligonucleotides eluting from a CAPLC® system, and with a MICROMASS® ZQ™ single-quadrupole mass spectrometer (available from Waters Corporation, Milford, Mass.) for analysis of peptides eluting from the ALLIANCE® bio-separations system.

Columns: XTERRA® C18 columns having ID and length dimensions respectively of 1.0 mm×50 mm, and sorbent particle size of 2.5 μm were used for some oligonucleotide separations. ATLANTIS™ dC18 columns having ID and length dimensions of 2.1 mm×150 mm, and sorbent particle size of 5 μm were used for some peptide separations. ATLANTIS™ dC18 columns having ID and length dimensions of 4.6 mm×100 mm, and sorbent particle size of 5 μm were used from some preparative peptide purifications (all columns available from Waters Corporation, Milford, Mass.)

Figure 2A:
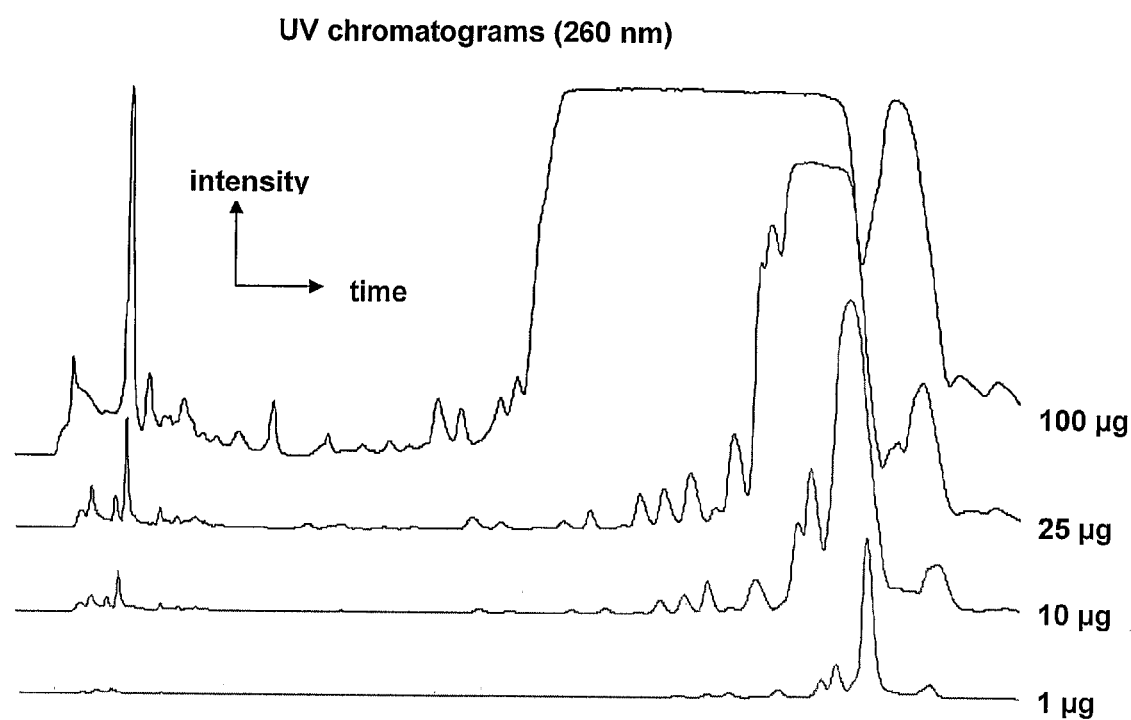
FIG. 2a is a graph of four UV chromatograms obtained from separations of an oligonucleotide sample corresponding to four different sample loads, in accordance with one embodiment of the invention.

FIG. 2a illustrates four UV chromatograms (260 nm wavelength absorption, coordinates of time and intensity of arbitrary units) obtained from separations of a 25-mer PS oligonucleotide, corresponding to four different sample loads (1 μg, 10 μg, 25 μg, and 100 μg.) The separations were obtained via ion-pair reversed-phase HPLC. The solvent gradient conditions were as follows: a linear gradient for 1 minute from 0-13% of mobile phase B followed by a linear gradient for 28 minutes from 13-20% of mobile phase B. The column ID was 1 mm, the temperature was 60° C., and the solvent flow rate was 23.6 μL/min.

As illustrated, UV detection of the chromatographic peaks of the PS oligonucleotide became saturated with increasing mass load, notably at the 100 μg load. For the 100 μg load, for example, the UV chromatogram indicates that a displacement wave of sample compounds has formed, but does not clearly indicate where, or if, boundaries exist between the separated compounds.

Figure 2B:
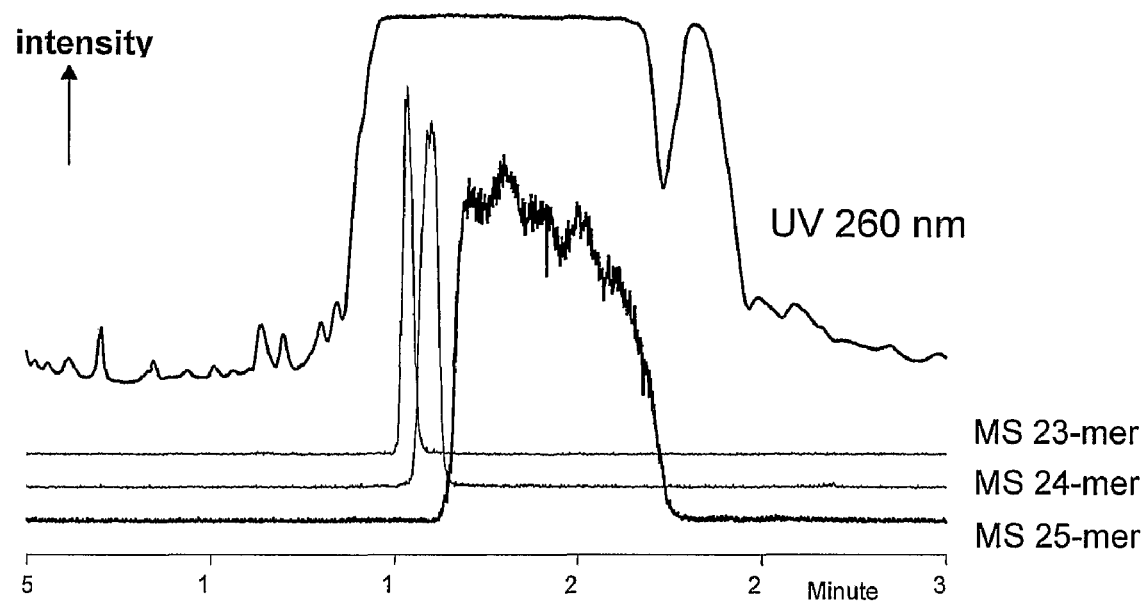

Now referring to FIG. 2b, mass-spectrometric data provides a relatively clear indication of both the good separation of compounds and an appropriate collection window for a target compound. FIG. 2b illustrates electro-spray ionization (ESI) mass-spectral ion chromatograms for three compounds (25-mer, 24-mer, and 23-mer) of the 100 μg load sample of FIG. 2a (for reference, FIG. 2b also includes the UV chromatogram from FIG. 2a.) The ion chromatograms were obtained by collecting a series of mass-spectrometric scans over a period of several minutes as the displacement train eluted from the column. Each scan was collected by scanning over a mass-to-charge ratio of 340 Da to 1500 Da in 1 sec.

As illustrated, the three compounds have slightly different retention times. The compounds, however, remain physically (and temporally) well separated in spite of both an overloaded sample and a solvent gradient, as observable via the mass-spectrometric data. As described above, however, the compounds are poorly resolved in the UV chromatogram. Thus, the mass-spectrometric data, in contrast to the UV-absorption data, are suitable for, for example, accurate identification of the eluting 25-mer compound for separation purposes when collection without major synthesis impurities, e.g., 24-mer and 23-mer, is desired.

As illustrated by this example, closely related compounds of some sample types have inherently close UV absorption peaks. For such sample compounds, in some circumstances, their associated UV peaks will have relatively sharp boundaries that still appear to overlap due to their close proximity. Mass-spectrometric data, however, readily distinguishes the compounds in response to their mass differences.

Thus, in contrast to some prior displacement-chromatographic methods, a target compound is caused to elute from a column and retain good separation from contiguous compounds in the displacement train without use of a separate displacer material.

Figure 3A:
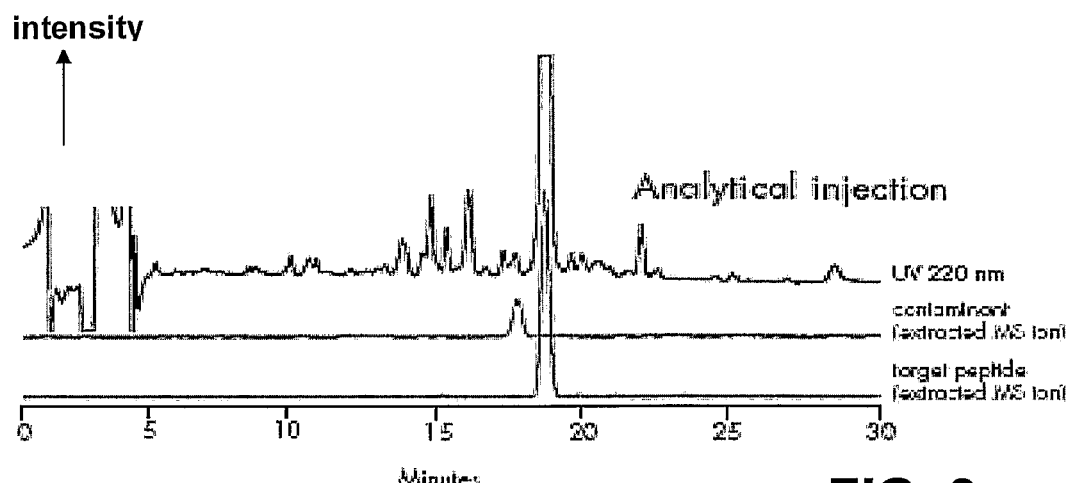
FIGS. 3a, 3b and 3c are graphs of UV-adsorption chromatograms and mass-spectral ion chromatograms obtained from synthetic peptide separations having sample loads respectively of 2 µg, 200 µg, and 1000 µg.
Figure 3B:
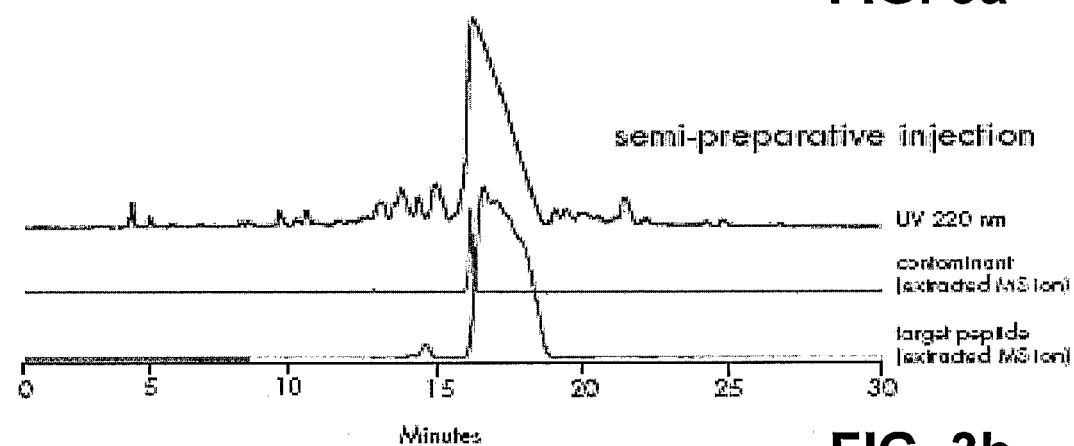
Figure 3C:
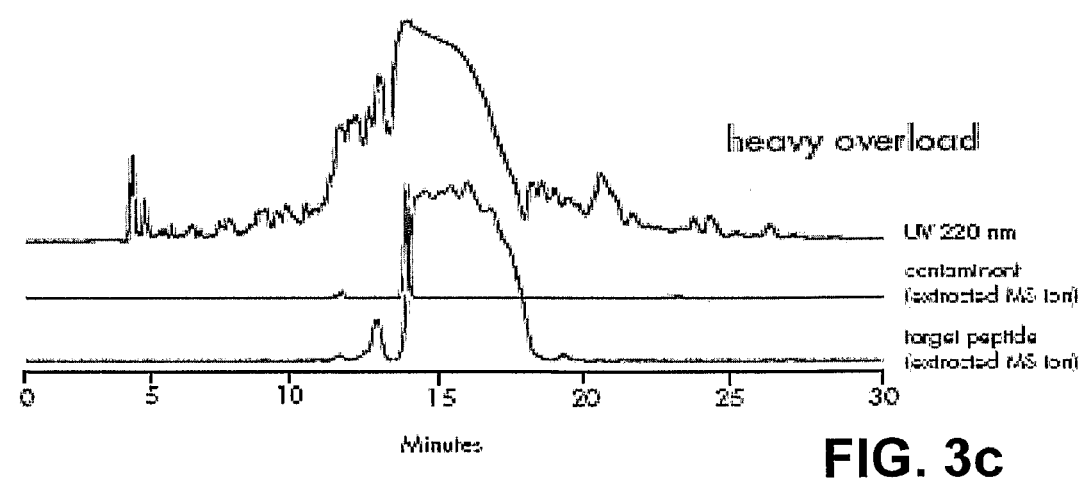

FIGS. 3a, 3b and 3c illustrate UV-adsorption chromatograms (220 nm wavelength) and mass-spectral ion chromatograms obtained from synthetic peptide separations having sample loads respectively of 2 μg, 200 μg, and 1000 μg. The sample had a peptide sequence (N to C terminus) of WLTGPQLADLYHSLMK, with a target peptide mass-to-charge ratio (m/z) value of 1873.2 Da (doubly charged=937.1 m/z) and a closely eluting synthesis contaminant at m/z=758.1 Da.

The separation was performed with the above-described analytical separation equipment, including a column with an ID of 2.1 mm. A solvent gradient had the following parameters: a linear gradient for 30 minutes from 18% to 42% of mobile phase B, and a flow rate of 0.2 mL/min. Temperature was at ambient. Mass-spectral data were obtain by scanning a m/z range from 300 Da to 2500 Da with a scan time of 2.2 sec. A series of spectra taken over an elution time of approximately 30 minutes provided the illustrated intensity versus time curves associated with the concentrations of the target and the contaminant eluting over time.

The sample loads of 2 μg, 200 μg, and 1000 μg in this example were respectively associated with an analytical injection, i.e., less than an overload threshold, a semi-preparative injection, i.e., near the threshold, and an overload condition. The decreasing retention times and increasing peak widths associated with increasing load indicate the formation of a displacement train as an overload threshold is attained and surpassed.

As illustrated, for overloaded conditions, the mass-spectrometric data provide a clear indication that the target and the impurity remain well separated under gradient elution. The data, as described above, in some embodiments of the invention, are responsively used to trigger collection of the target and/or other compounds of a separation. For example, referring again to FIG. 3c, the rising edge of the target mass-spectrometric peak is used in some cases to trigger collection of the target and/or the declining edge of the target mass-spectrometric peak is used to cease collection of the target. Alternatively, for example, the observed end of the impurity peak is used to trigger collection of the target.

In the above-described manner, the target is collected with a purity of, for example, approximately 95% to 98% or 99%, or better, after a single chromatographic separation process. Moreover, some embodiments of the invention provide, in response to spectroscopic data, automated collection of one or more target compounds and/or other compound(s) of a separation.

Figure 4:
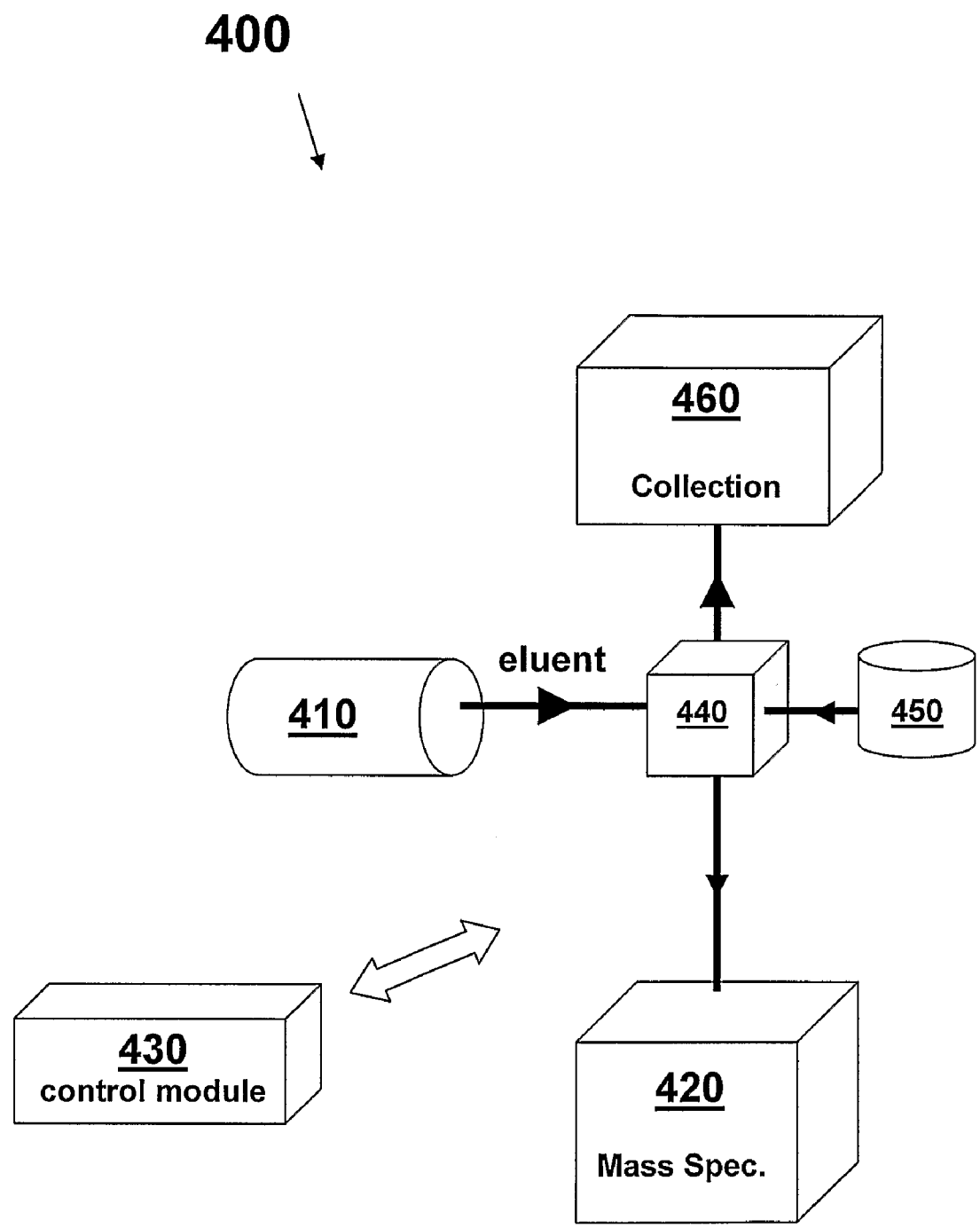
FIG. 4 is a block diagram of an embodiment of a purification system, in accordance with one embodiment of the invention.
Figure 5:
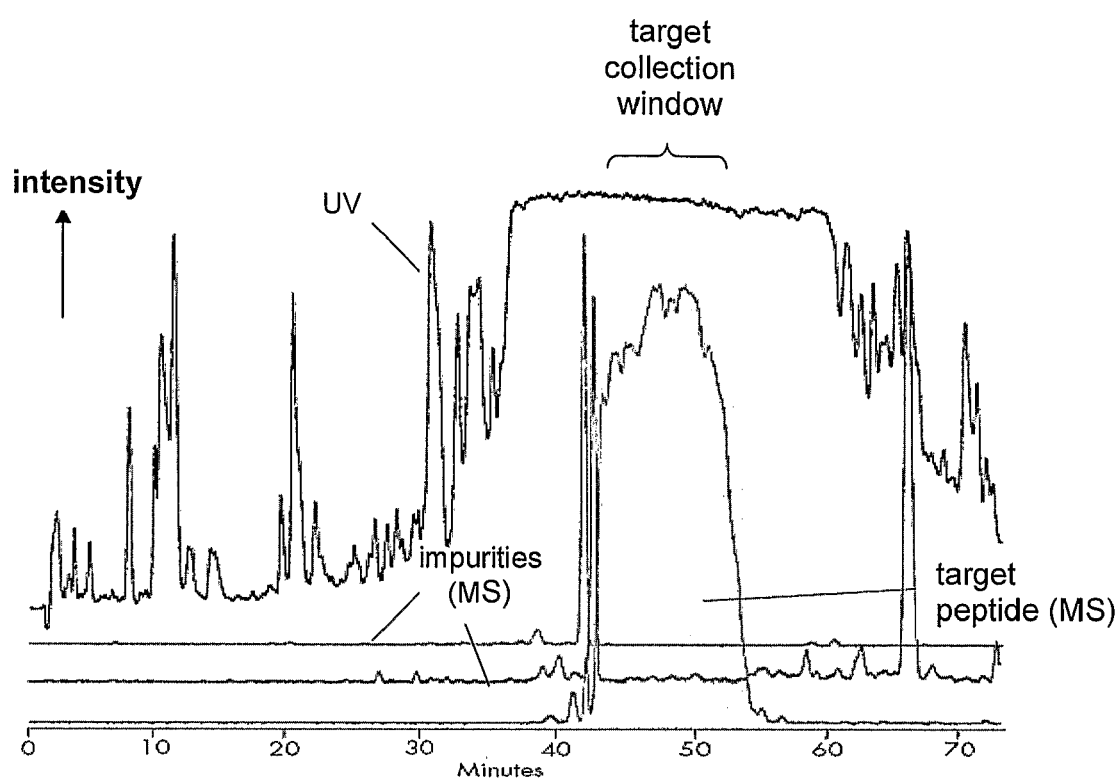
FIG. 5 is a graph of a UV chromatogram and mass-spectral ion chromatograms obtained from a 20 mg load of a synthetic peptide associated with FIGS. 3a, 3b, and 3c.

Now referring to FIG. 4 and to FIG. 5, examples of automated purification systems are described. Via exploitation of automation, through use of mass-spectrometric data to trigger collection of desired separation compounds, a large number of samples are efficiently processed. For example, a mass spectrometer is configured to detect an expected molecular weight of a target in a sample, and to direct the collection of the purified target in response to detection of its expected molecular weight.

FIG. 4 is a block diagram of an embodiment of a purification system 400, in accordance with one embodiment of the invention. The system includes a chromatographic module 410, a mass-spectrometer module 420, a control unit 430, an eluent flow-control unit 440, a diluent supply 450, and a collection unit 460.

The eluent flow-control unit 440 receives eluent from the chromatographic component 410, and directs portions of the eluent to the collection module 460 and to the mass-spectrometer module 420. The eluent flow-control unit 440 is also in fluid communication with the diluent supply to permit mixing of a diluent with the portion of eluent directed to the mass-spectrometer module 420.

The chromatographic module 410 includes any suitable chromatography instrument(s), including known instruments, such as column-based instruments. Suitable columns include columns known to one having ordinary skill in the chromatographic arts. The column can be formed from, for example, metallic or insulating materials. Suitable materials include known materials such as steel, fused silica, or lined materials. The column can include more than one column, disposed in serial and/or parallel configurations. For example, the column can be a capillary column and can include multiple capillary tubes.

The control unit 430 is in data communication with other components of the system 400 via wired and/or wireless means, such as those known in the data-communication arts. The control unit 430 receives process data, for example, from the mass-spectrometer module 420, and provides control signals to other components, for example, the flow-control unit 440. The control unit 430 is configured to support automation of sample purification by the purification system 400. The control unit 430, in various illustrative embodiments, is implemented in software, firmware, and/or hardware (e.g., as an application-specific integrated circuit), and includes, if desired, a user interface. The control unit 430 includes and/or is in communication with storage component(s).

Suitable implantations of the control unit 430 include, for example, one or more integrated circuits, such as microprocessors. A single integrated circuit or microprocessor in some alternative embodiments includes the control unit 430 and other electronic portions of the system 400. In some embodiments, one or more microprocessors implement software that enables the functions of the control unit 430. In some embodiments, the software is designed to run on general-purpose equipment and/or specialized processors dedicated to the functionality herein described.

In some implementations of the system 400, the control unit 430 includes a user interface to support interaction with the control unit 430 and/or other portions of the system 400. For example, the interface is configured to accept control information from a user and to provide information about the system 400 to a user. The user interface is used, for example, to set system control parameters and/or to provide diagnostic and troubleshooting information to the user. In one embodiment, the user interface provides networked communication between the system 400 and users located either local to the operating environment or remote from the operating environment. The user interface in some implementations is used to modify and update software.

The flow-control unit 440 is configured to direct all or part of an eluent to the collection module 460 and/or the mass-spectrometer module 420. For example, during elution of a sample's displacement train, a small portion of the eluent, for example, approximately 1% by volume, is directed by the flow-control unit 440 to the mass-spectrometer module 420. Mass spectrometry is then performed on the diverted eluent; in response to detection of a m/z value of a desired target compound, the control unit 430 instructs the flow-control unit 440 to direct eluent to the collection module 460 and/or instructs the collection module 460 to begin to collect the eluent.

In one embodiment of the invention, the control unit includes a memory for storing instructions that, when executed, cause implementation of any one of the methods described herein. For example, in one embodiment, the instructions cause the system 400 to implement the following steps, without further human intervention: injecting an overloaded amount of a sample; flowing a solvent having a time-varying composition; and collecting a target material in response to mass-spectrometric data associated with the portion of the eluent.

In view of the description of illustrative embodiments provided herein, it will be apparent to one having ordinary skill in the separation arts that various other configurations and implementations of control units can be utilized in other embodiments of the invention to provide automated control of target compound collection.

Although some specific, illustrative mobile phases and associated gradients are described herein, other suitable mobile phases and gradients are used in alternative processes, in accordance with other embodiments of the invention. In some embodiments of the invention, for example, mobile phases are selected for their compatibility with mass spectrometry. Some solvents are directly compatible, requiring no dilution prior to mass spectrometry. Others are indirectly compatible, requiring some amount of dilution prior to mass spectrometry. For example, without dilution, some solvents reduce the detection sensitivity of a mass spectrometer.

An example of a directly compatible solvent is a mobile phase A of 0.1% TFA in water, in combination with a mobile phase B of 0.08% TFA in ACN. This solvent is used in some embodiments of the invention to separate, for example, peptide samples.

An example of an indirectly compatible solvent is a mobile phase A including HFIP and TEA, in combination with a mobile phase B of MeOH. A portion of eluent in this case is advantageously diluted, by, for example, a factor of 10, prior to mass spectrometry. This solvent is used in some embodiments of the invention to separate, for example, oligonucleotide samples.

A diluent is selected, for example, to provide improved compatibility with mass spectrometry. Any suitable material, including known materials, may be used as a diluent. For example, one diluent includes approximately 50% ACN and approximately 50% water. More generally, in some embodiments, a diluent includes approximately 20% to approximately 50% of an organic compound an approximately 50% water.

Referring next to FIG. 5, an example an automated analysis is described. FIG. 5 illustrates a UV-adsorption chromatogram (220 nm wavelength, arbitrary intensity units) and mass-spectral ion chromatograms obtained from a 20 mg load of the synthetic peptide associated with FIGS. 3a, 3b, and 3c. Three chromatograms obtained by mass spectrometry are shown (arbitrary intensity units,) one for the target peptide and two for sample impurities.

The separation was performed in a column having an ID of 4.6 mm. The solvent gradient had an initial hold at 10% mobile phase B for 1 minute, followed by a linear gradient during which the mobile phase B composition of the solvent was increased from 10% to 50% during 90 minutes no processing. The solvent flow rate was 1.0 mL/min. The column was held at ambient temperature. Fraction collection for the target peptide was triggered by selected-ion monitoring of a mass weight of 1874.0 Da. Re-injection of the collected portion indicated that the initially collected portion had a purity of approximately 98%, while the purity of the target in the original sample was approximately 86%.

Variations, modifications, and other implementations of what is described herein will occur to those of ordinary skill in the art without departing from the spirit and the scope of the invention as claimed. For example, various embodiments of the invention are suitable for purification of a variety of materials including, but not limited to pharmaceuticals, antigens, affinity tags, diagnostics, RNAi, oligo-probes, and small-molecule samples, such a phenyl-group samples. Accordingly, the invention is to be defined not by the preceding illustrative description but instead by the spirit and scope of the following claims.

What is claimed is:

1. A method for extracting at least one target compound from a sample comprising a plurality of compounds, the method comprising:
   injecting an overloaded amount of the sample into a chromatographic conduit, and, in response, forming a displacement train in which the at least one target compound is substantially separated from a contiguous compound of the plurality of compounds; and
   flowing, through the conduit, a solvent having a time-varying composition, and, in response, causing an eluent comprising the at least one target compound to elute from an exit orifice of the conduit while the at least one target compound remains substantially separated from the contiguous compound.

2. The method of claim 1, further comprising obtaining, from a portion of the eluent, spectroscopic data that identifies a boundary between the at least one target compound and the contiguous compound.

3. The method of claim 2, wherein obtaining spectroscopic data comprises obtaining mass-spectroscopic data.

4. The method of claim 2, further comprising collecting the at least one target compound in response to the identified boundary.

5. The method of claim 4, wherein the collected at least one target compound has a purity of at least about 98%.

6. The method of claim 4, wherein the collected at least one target compound has a yield of at least about 80%.

7. The method of claim 6, wherein the collected at least one target compound has a purity of at least about 95%.

8. The method of claim 2, wherein obtaining comprises identifying a collection window associated with the at least one target compound, and further comprising collecting the at least one target compound in response to the identified collection window.

9. The method of claim 1, wherein flowing the solvent comprises causing the time-varying composition to have at least a first linear gradient.

10. The method of claim 9, wherein flowing the solvent further comprises causing the time-varying composition to have a second linear gradient subsequent to the linear gradient.

11. The method of claim 1, wherein flowing the solvent comprises causing the time-varying composition to have an isocratic portion while injecting the overloaded sample.

12. The method of claim 1, wherein the overloaded amount is associated with a ratio, of mass-to-area of conduit cross section, of greater than about 1.0 mg/mm$^2$.

13. The method of claim 1, wherein the displacement train is a self-displacement train.

14. The method of claim 1, wherein the overloaded amount is at least sufficient to cause the at least one target compound in the displacement train to saturate a response of a UV detector such that the at least one target compound and the contiguous compound cannot be sufficiently resolved via UV absorbance spectrometry.

15. The method of claim 1, wherein the solvent comprises a first mobile phase comprising water, and a second mobile phase comprising acetonitrile.

16. The method of claim 15, wherein each of the first mobile phase and the second mobile phase further comprise trifluoroacetic acid.

17. The method of claim 16, wherein flowing the solvent comprises causing the time-varying composition to vary between about 15% and about 50% of the mobile-phase B.

18. The method of claim 1, wherein the solvent comprises a mobile-phase A comprising hexafluoroisopropanol and triethylamine, and a mobile-phase B comprising MeOH.

19. The method of claim 18, wherein flowing the solvent comprises causing the time-varying composition to vary between about 0% and about 25% of the mobile-phase B.

20. The method of claim 1, wherein the at least one target compound is more hydrophilic than the contiguous compound.

21. The method of claim 1, further comprising injecting a displacer material into the chromatographic conduit after injecting the overloaded amount of the sample.

\* \* \* \* \*